United States Patent [19]

Madgavkar et al.

[11] 4,394,296

[45] Jul. 19, 1983

[54] BORON TRIFLUORIDE-WATER-SILICA CATALYST

[75] Inventors: Ajay M. Madgavkar, Irvine, Calif.; Harold E. Swift, Gibsonia, Pa.

[73] Assignee: Gulf Research & Development Company, Pittsburgh, Pa.

[21] Appl. No.: 289,456

[22] Filed: Aug. 3, 1981

Related U.S. Application Data

[63] Continuation-in-part of Ser. No. 104,415, Dec. 17, 1979, Pat. No. 4,308,414.

[51] Int. Cl.$^3$ .......................... B01J 21/02; B01J 37/00
[52] U.S. Cl. ...................................... 252/433; 252/420
[58] Field of Search ................................ 252/420, 433

[56] References Cited

U.S. PATENT DOCUMENTS

| | | | |
|---|---|---|---|
| 2,284,554 | 5/1942 | Beyerstedt | 252/433 X |
| 2,296,370 | 9/1942 | Slotterbeck | 252/433 X |
| 2,836,634 | 5/1958 | Lee et al. | 252/433 X |
| 3,109,041 | 10/1963 | Child et al. | 585/525 X |
| 3,190,936 | 6/1965 | Child et al. | 585/525 |
| 3,855,342 | 12/1974 | Huang et al. | 252/433 X |
| 3,997,621 | 12/1976 | Brennan | 260/683.15 B |

FOREIGN PATENT DOCUMENTS

| | | | |
|---|---|---|---|
| 50-62927 | 5/1975 | Japan | 252/433 |
| 550711 | 1/1943 | United Kingdom | 252/433 |

*Primary Examiner*—Delbert E. Gantz
*Assistant Examiner*—William G. Wright
*Attorney, Agent, or Firm*—Deane E. Keith; Forrest D. Stine; Donald L. Rose

[57] ABSTRACT

A three-component catalyst is prepared comprising a particulate silica adsorbent with boron trifluoride and water adsorbed on the silica. The silica-water-boron trifluoride catalyst is used in hydrocarbon conversion reactions such as the oligomerization of 1-decene to a product predominating in the trimer and tetramer.

7 Claims, No Drawings

BORON TRIFLUORIDE-WATER-SILICA CATALYST

This patent application is a continuation-in-part of U.S. patent application Ser. No. 104,415, filed Dec. 17, 1979, now U.S. Pat. No. 4,308,414.

SUMMARY OF THE INVENTION

A three-component catalyst comprising boron trifluoride, water and silica is an active boron trifluoridecontaining catalyst which is useful in hydrocarbon conversion reactions such as the oligomerization of alpha-olefins.

DESCRIPTION OF THE INVENTION

In recent years the higher alpha-olefins have been oligomerized to liquids useful as lubricants and related functional fluids using as the catalyst a complex formed from boron trifluoride and a suitable polar compound selected from water, alcohols, ethers, carboxylic acids, carboxylic acid esters and the like. Although these coordination compounds of boron trifluoride are very effective oligomerization catalysts for the higher alpha-olefins, they possess a significantly reduced activity after they have been used in the oligomerization reaction. Their recovery and reactivation has not been entirely practical and economical. Therefore, this inability to successfully reuse the catalyst requires the substantial continuing expense of fresh catalyst and co-catalyst. Furthermore, this inability to reuse the catalyst presents additional costs for the waste treatment and disposal of the spent catalyst, and this disposal problem increases the possibility of environmental contamination.

The coordination compound of boron trifluoride and water is also catalytically active for a variety of other hydrocarbon conversion reactions. U.S. Pat. No. 2,284,554 discloses that boron trifluoride water catalysts can be employed in organic condensation reactions such as the alkylation of isoparaffins and aromatic compounds with olefins, in the polymerization and copolymerization of mono- and diolefins, in the esterification of carboxylic acids with alcohols, in the etherification of alcohols with alkyl halides, and in various other types of hydrocarbon conversion reactions. This patent also describes the deactivation of the boron trifluoride.water catalyst during the catalyzed reaction. In contrast with this successful combination of water and boron trifluoride in a catalyst, U.S. Pat. Nos. 3,109,041 and 3,190,936 disclose that water or moisture is undesirable in the reactor and must be removed from the olefin feed when boron trifluoride adsorbed on silica is used as a catalyst for the polymerization of olefins, such as isobutylene.

Surprisingly, we have discovered that all three components, namely, boron trifluoride, water and silica, can be combined to form a catalyst having good activity and which is resistant to aging and loss of activity for prolonged periods of use in hydrocarbon conversion reactions. The boron trifluoride can be readily recovered from the reaction product for reuse in the process at its original activity without the significant loss in activity that is experienced with the two-component complex of boron trifluoride with water. As a result, catalyst and waste treatment costs are minimized and disposal and environmental problems are substantially avoided.

We have discovered that our noval three-component catalyst is of particular utility in the oligomerization of 1-olefins and will describe this catalyst in more detail in connection with oligomerization reactions to exemplify its use. The silica, comprising one of the components in our three-component catalyst system functions as a solid adsorbent in the reaction system. It can be positioned in the oligomerization reactor as a bed for flow-through contact with the reaction liquid. Alternatively, the silica can be maintained as a slurry in the reaction liquid by suitable agitation in a batch or continuous reaction. When the reaction vessel is pressured with boron trifluoride, the second component of our catalyst system, a substantial quantity of the boron trifluoride is adsorbed by the silica adsorbent to form an active oligomerization catalyst. Since boron trifluoride tends to desorb from the silica, a suitable boron trifluoride pressure and a suitable concentration of boron trifluoride in the reaction liquid is maintained during the oligomerization reaction to insure that the catalytically active silica-boron trifluoride combination is maintained throughout the course of the oligomerization reaction.

However, we have observed that this two-component catalyst comprising the silica and the boron trifluoride gradually loses activity after a period of continued use, which aging cannot be conveniently corrected by increasing the boron trifluoride pressure. We believe that this aging is the result of gradual physical and chemical changes in the silica-boron trifluoride catalyst as it is being used. Unexpectedly, we have discovered that this aging can essentially be prevented if a minute amount of water is fed to the reactor in the 1-olefin feed. This water is also adsorbed by the silica adsorbent to form the three-component catalyst system of our invention. Not only does this three-component system prevent aging of the catalyst, but surprisingly, we have further discovered that a silica-boron trifluoride catalyst which has aged in an absence of water in the reaction feed can be regenerated to substantially its original activity merely by introducing the requisite amount of water with the feed olefin and continuing the reaction.

We have further discovered that the overall conversion of the 1-olefin is significantly improved without substantial change in the selectivity to the various oligomer fractions by the presence of our three-component catalyst in comparison with the water-free catalyst. As a result of this greater catalyst activity resulting from the use of water, the process can be operated at a greater throughput of the 1-olefin feed as determined by the liquid hourly space velocity. Another benefit in this greater catalyst activity is that the process can be operated with less boron trifluoride in the catalyst and therefore less boron trifluoride fed to the reactor.

We have determined that the beneficial results that are obtained in our process by the use of water in association with the silica and boron trifluoride catalyst components are obtained within the solubility limits of the water in the 1-olefin. For example, we have found that the upper solubility limit of water in 1-decene is from 100 to 130 ppm. (parts by weight of water per million parts by weight of 1-decene) at 25° C. In general, an upper limit of 40 or 50 ppm. water in the olefin feed is all that is generally necessary to obtain the full benefits of the three-component catalyst system in the oligomerization reaction. A minimum amount of water is necessary in order for its use to be advantageous. For example, although improvement in conversion and in the maintenance of catalyst activity can be observed when the 1-olefin feed contains about five ppm. water it is preferred that the feed olefin contain at least about ten ppm. water for significant improvement and at least 20 or 25 ppm. water is desired for substantial improvement in conversion and maintenance of catalyst activity.

As is the case with the prior art oligomerization, 1-decene is the most preferred alpha-olefin for preparing synthetic lubricants and related functional fluids using our novel catalyst. However, 1-olefins having from three to 12 carbon atoms and preferably eight to 12 carbon atoms, or mixtures thereof, can also be used. The straight chain, normal 1-olefins are preferred, however, branched chain 1-olefins can comprise a portion or all of the 1-olefin feed. When a 3- or 4-carbon olefin is used, it is generally preferred that this lower olefin be cooligomerized with at least about 20 mol percent of one or more of the higher olefins in order to obtain the desired oligomer mixture.

In its broadest aspect, the lubricating oil range to which the process is directed varies between about 20 and about 50 carbon atoms, and more particularly between about 24 and 42 carbon atoms, and most preferably about 30 to about 40 carbon atoms. The process is, therefore, preferably carried out under appropriate conditions to obtain the maximum oligomer selectivity within the desired range of carbon numbers. One of the particular benefits of our three-component catalyst system is that high product selectivity within the lubricating oil range is readily obtained and under appropriate conditions the selectivity is even enhanced. Since it is difficult to separate or even determine by analysis the different oligomer fractions having about 50 carbon atoms and higher, reference herein to an oligomer fraction having about 50 carbon atoms is intended to include the possible presence of minor amounts of one or more oligomer fractions having a higher number of carbon atoms.

The three-component catalyst is preferably used as a fixed bed of relatively uniformly sized particles in a flow-through reactor. We have determined that the external surface area of the catalyst is a more significant factor with regard to catalyst activity than its pore volume. As a result, the particle size can be of particular significance. In general, the smaller the particle size the greater the activity at constant catalyst volume, however, a catalyst bed formed from too finely sized particles tends to restrict the flow of the reaction stream as indicated by a significant pressure drop across the catalyst bed. For these reasons the particle size of the catalyst is preferably at least about 100 mesh (0.15 mm.) in particle size, and most preferably at least about 50 mesh (0.3 mm.). The maximum particle size is preferably about 3 mesh (6.7 mm.) and most preferably about 10 mesh (2.0 mm.). However, useful oligomer products can be prepared with silica adsorbent outside these limits of particle size. When a slurry of the three-component catalyst is used in a reactor, not only the particle size but also the amount of the catalyst exerts a significant effect on the rate of reaction.

The reaction temperature also exerts a significant effect on the reaction. As the temperature increases at constant contact time, both the conversion and the selectivity to oligomers higher than the dimer decreases while the amount of the dimer increases. For this reason it is desirable that the maximum reaction temperature be about 150° C., preferably no higher than about 100° C. and most preferably no higher than about 50° C. On the other hand although the reaction can be carried out at a temperature as low as about −50° C., it is preferred that the minimum operating temperature be at least about −10° C. We believe that the temperature affects the solubility of the boron trifluoride in the reaction liquid and also affects the adsorption of both the water and the boron trifluoride on the silica adsorbent and that these cumulative effects help to cause the inverse relationship of temperature with conversion. We have found, in general, that a temperature gradient exists across the catalyst bed during the reaction by as much as 10° C. or more. The term reaction temperature therefore refers to the highest temperature or "hot spot" temperature in the catalyst bed. On the other hand a uniform temperature will be present in a slurry reactor.

Desirably the boron trifluoride gas and the 1-olefin are either jointly introduced into the inlet end of the reactor or alternatively the boron trifluoride can be injected into the 1-olefin feed stream immediately prior to its introduction into the reactor. This procedure is followed to essentially eliminate any direct reaction in the olefin feed line of the boron trifluoride with the water dissolved in the olefin and/or avoid undesired and uncontrolled oligomerization in the olefin feed line prior to the reactor itself. Furthermore, this procedure permits the boron trifluoride and the water to be adsorbed by the silica adsorbent within the reactor to form the three-component catalyst system in the desired manner.

Since boron trifluoride continuously desorbs from the silica during the course of the reaction, it is necessary to feed boron trifluoride to the reaction inlet to insure that sufficient boron trifluoride is present in the catalyst for the oligomerization reaction. The adsorption and desorption of the boron trifluoride is affected by many operating variables including temperature, pressure, moisture content, nature and particle size of the silica adsorbent, the composition of the feed and the reaction mixture, and the like. The minimum feed rate of the boron trifluoride will therefore depend on the particular operating conditions in any specific situation.

Typically, the boron trifluoride feed rate is at least equal to its solubility in the reaction liquid at the particular conditions of operation, and preferably is in excess of its solubility in the reaction liquid. The solubility of the boron trifluoride in the reaction liquid is significantly affected by the partial pressure of boron trifluoride in the gas phase. We have also found that the boron trifluoride partial pressure exerts a significant effect on the amount of boron trifluoride adsorbed by the silica adsorbent and on the resulting catalyst activity. As a result, variations in pressure result in significant variations in conversion but with only moderate variations in product selectivity. Pure boron trifluoride gas can be utilized or it can be used in admixture with an inert gas such as nitrogen, argon, helium, and the like. When used as a mixture, it is preferred that it comprise at least about 10 mol percent of the gas mixture.

Because of the many variables involved, as indicated, it is difficult to specify a feed rate for the boron trifluoride for any particular set of operating variables, although it can be stated that, in general, it will be at least about 0.1 weight percent of the 1-olefin. It is more meaningful to indirectly indicate the amount of boron trifluoride fed to the reactor by specifying the partial pressure of boron trifluoride in the reactor. Even though the oligomerization reaction can be carried out at atmospheric pressure when using pure boron trifluoride, we find it desirable to maintain a partial pressure of boron trifluoride in the reactor of at least about 10 psig. (0.17 MPa) for suitable catalyst for activity and preferably at least about 50 psig. (0.44 MPa) for superior catalyst activity. Partial pressures of boron trifluoride as high as about 500 psig. (3.55 MPa) and higher, such as about 1,000 psig. (7.03 MPa), can be utilized but it is preferred that an operating partial pressure of about 250 psig. (1.83 MPa) not be exceeded. The elevated pressures are, in general, avoided where their possible benefits in improved catalyst activity are outweighed by the added boron trifluoride and process costs. Lower operating pressures also appear to result in an improved product quality, possibly resulting from reduced isomerization.

When the fixed bed reactor is used, suitable results can be obtained with a relatively high throughput of the liquid reactant olefin. In fact, we find that conversion of 1-olefin is only moderately decreased as the space velocity of the reactant liquid is increased. In the case of a 1-decene feed an increase in space velocity results in an increase in the dimer and a corresponding decrease in the higher oligomer fractions. The oligomerization reaction in a fixed bed can conveniently be carried out within the broad range of liquid hourly space velocities, that is, the volume of the liquid feed per volume of catalyst per hour, of between about 0.1 and 50 hr.$^{-1}$, but preferably the reaction is carried out within the range of about 0.5 and about 10 hr.$^{31\ 1}$. These ranges for space velocity are also applicable with a flow-through slurried catalyst system.

Since the oligomerization reaction involves a series of competing reactions, monomer with monomer, monomer with dimer, dimer with dimer, monomer with trimer, etc., resulting in a series of product oligomer fractions, the particular reaction conditions utilized will depend on the 1-olefin feed that is used and the product oligomer, fraction or fractions, that is desired. Although it is preferred that the reaction be carried out at maximum conversion and optimum selectivity to desired products, such may not be possible. However, the overall selectivity may be substantially improved if those oligomer fractions lower than the desired oligomer fractions are recovered from the product stream and recycled to the feed stream for further reaction. Since the oligomer fractions which are heavier than the desired fractions represent a process loss, it may be desirable to operate the oligomerization reaction under conditions which minimize the undesired heavier fractions even though this may increase the amount of product recycle.

The expression reaction liquid as used herein refers to the alpha-olefin monomer or mixture of monomers, any inert solvent, if present, and the oligomer products which will be present once reaction has started. It is possible to carry out the reaction in the presence of up to about 80 percent, preferably up to about 60 percent, of a suitable inert solvent. Suitable solvents can be used for temperature control and for product control. Such solvents tend to slow down the various reaction rates and can be utilized in conjunction with the different variables to control the course of the reaction and the nature of the reaction products. Suitable solvents can be selected from the aliphatic hydrocarbons such as pentane, hexane, heptane, and the like; and aromatic hydrocarbons, such as benzene, toluene, chlorobenzene, and the like. The solvent, if utilized, should be liquid at reaction conditions and should be substantially lower in boiling point than any other component to simplify separation upon completion of the reaction.

In the slurried catalyst system, the three-component catalyst is maintained as a slurry in the reaction liquid by suitable agitation. In the continuous slurry procedure, a suitable porous plate is positioned between the reaction liquid and the reactor outlet. A continuous stream of reaction product is removed at a rate to provide a predetermined desirable average residence time in the reactor. Since the filter plate prevents the egress of the powdered catalyst, the product stream is free of solids. As the product is removed, make-up alpha-olefin is injected into the reactor inlet to provide a constant liquid volume in the reactor. The particle size of the silica, the openings in the filter plate and the vigor of the agitation are appropriately intercorrelated to insure that the catalyst particles neither block the filter openings nor cake up on the filter plate. The batch method can be carried out in the same equipment with the catalyst remaining in the reactor between batches or if a filter plate is not used, the slurry can be removed from the reactor at the termination of a batch, filtered and the catalyst returned for the next batch.

The reaction product which is removed from the reactor contains unreacted feed olefin, the various product oligomer fractions, any impurities which were originally present in the feed olefins, inert solvent when used, and dissolved boron trifluoride gas. The amount of boron trifluoride in the product liquid will, in general, fall within the range of between about 0.1 and about 20 weight percent depending upon the amount of boron trifluoride that is fed to the reactor and usually in the lower end of this range. This boron trifluoride can be readily separated from the liquid product in nearly quantitative yield by subjecting the product solution to a vacuum at about 100° C., by heating the product liquid to 100° C. and bubbling nitrogen through the liquid, or by any other appropriate procedure. This separated boron trifluoride is reusable in the process without any change in the activity of the three-component catalyst system. Traces of the boron trifluoride can be removed from the reaction product with a water wash. The liquid reaction product can then be hydrogenated to eliminate double bond unsaturation either before or after its separation into the desired fractions.

DESCRIPTION OF PREFERRED EMBODIMENTS

The following experiments were carried out in a vertically mounted, stainless steel reactor one-half inch (12.7 mm.) in internal diameter and two feet (61 cm.) in length. A 20-inch (51 cm.) thermocouple well was positioned within the reactor to determine the temperature at different locations within the catalyst bed. The 1-decene reactant was pumped into the bottom of the reactor and dry boron trifluoride was injected into the 1-decene feed line immediately before it entered into the reactor. The product stream was collected in a 500 cc. receiver.

The 1-decene typically contained 1.5 percent saturates and other olefins. The solid adsorbent was Davison Grade 59 silica having a B.E.T. area of about 250 m$^2$/g, which was calcined at 1,000° F. (538° C.) and sized to the desired mesh size. The reactor was packed with 60 cc. of the silica and boron trifluoride gas was injected into the reactor and maintained under pressure for 30 minutes before each series of experiments. Product analysis was carried out with a liquid or gas chromatograph as appropriate. The flow rate of the boron trifluoride gas in the following examples has been standardized to one atmosphere pressure and a temperature of 60° F. (15.6° C.).

EXAMPLE 1

This example which utilized dry 1-decene and an excess of boron trifluoride demonstrated catalyst aging as evidenced by a substantial reduction in the percent conversion of the 1-decene feed over a relatively short period of time. The reactor contained 60 cc. of 40/50 mesh (0.3 to 0.42 mm.) silica. The 1-decene was fed into the bottom of the reactor at a rate of 45 cubic centimeters (cc.) per hour (LHSV=0.75 hr$^{-1}$) and the boron trifluoride was injected into the 1-decene feed line at the rate of 11.4 cc. per minute, which was 6.15 weight percent boron trifluoride based on the 1-decene. The reactor was operated at an outlet pressure of 250 psig. (1.83 MPa). After operating for three hours to insure stable operation, analyses of the reaction products were begun. The temperature in the catalyst bed began to rise moderately in the 49th hour, which was believed to be the cause of a shift in the product selectivity. The results are set out in Table I.

TABLE I

| Hours | Max. Temp. °C. | Conv. % | Selectivity | | |
|---|---|---|---|---|---|
| | | | $C_{20}$, % | $C_{30}$, % | $C_{40}$, % |
| 3 | 29 | 88.1 | 38.6 | 54.8 | 5.75 |
| 12 | 31 | 84.8 | 37.8 | 49.6 | 10.0 |
| 20 | 27 | 80.8 | 36.8 | 55.5 | 6.5 |
| 32 | 30 | 74.7 | 41.7 | 53.2 | 5.1 |
| 40 | 27 | 66.5 | 42.1 | 54.0 | 3.9 |
| 54 | 36 | 58.1 | 50.3 | 46.6 | 3.0 |

EXAMPLE 2

The experiment of the preceding example was continued in all details except that the feed of boron trifluoride was cut in half to 5.70 cc. per minute. However, after about four hours, the dry 1-decene was replaced with 1-decene which contained 28 ppm. water (the average of two analyzed samples). After conditions in the reactor stabilized, the conversion increased to its original value and stayed there for about 20 additional hours as set out in Table II.

TABLE II

| Hours | Max. Temp. °C. | Conv. % | Selectivity | | |
|---|---|---|---|---|---|
| | | | $C_{20}$, % | $C_{30}$, % | $C_{40}$, % |
| 1 | 36 | 57.8 | 48.4 | 47.8 | 3.7 |
| 10 | 28 | 80.6 | 45.0 | 48.4 | 6.6 |
| 16 | 27 | 83.0 | 44.5 | 51.2 | 3.8 |
| 22 | 27 | 87.7 | 42.1 | 52.8 | 5.1 |
| 30 | 27 | 88.2 | 39.3 | 49.7 | 9.1 |

EXAMPLE 3

In this experiment the reactor contained 60 cc. of a fresh batch of 40/50 mesh (0.3 to 0.42 mm.) silica which had been pretreated with boron trifluoride under pressure. The 1-decene contained 42 ppm. water and was fed to the reactor at a rate of 300 cc. per hour which is a liquid hourly space velocity of 5.0 hr$^{-1}$. Boron trifluoride gas was fed to the 1-decene immediately prior to the reactor at a rate of 38.8 cc. per minute, which was 3.14 weight percent boron trifluoride based on the 1-decene. The reactor outlet was operated at 150 psig. (1.14 MPa). The hot spot temperature in the reactor rose for the first several hours dropping after about eight hours to steady state operation. The results of 43 hours of operation are set out in Table III.

| Hours | Max. Temp. °C. | Conv. % | Selectivity | | |
|---|---|---|---|---|---|
| | | | $C_{20}$, % | $C_{30}$, % | $C_{40}$, % |
| 7 | 52 | 87.8 | 19.7 | 53.4 | 18.9 |
| 19 | 18 | 87.9 | 21.4 | 65.0 | 13.1 |
| 27 | 27 | 88.1 | 22.8 | 62.6 | 11.5 |
| 35 | 20 | 89.2 | 23.9 | 62.1 | 12.8 |
| 43 | 21 | 90.6 | 22.8 | 61.8 | 13.7 |

EXAMPLE 4

A series of experiments were conducted to determine the effect of reactor pressure on catalyst activity as determined by the conversion of 1-decene and on product selectivity. A fresh 30 cc. batch of the 40/50 mesh silica was placed in the reactor and was treated with boron trifluoride gas at 240 psig. (1.76 MPa) for 30 minutes. The 1-decene was fed to the reactor at a rate of 150 cc. per hour (LHSV=5.0 hr$^{-1}$) and the boron trifluoride was fed at a rate of 19.38 cc. per minute (3.14 weight percent). The results are set out in Table IV in which the pressure is the outlet pressure and the temperature is the hot spot temperature in the catalyst bed.

TABLE IV

| Pressure, psig. (MPa) | Temp., °C. | $H_2O$ ppm. | Conv. % | Selectivity | | |
|---|---|---|---|---|---|---|
| | | | | $C_{20}$, % | $C_{30}$, % | $C_{40}$, % |
| atm. | −2 | 24 | 24.7 | 32.8 | 59.4 | 6.9 |
| 50(0.44) | 1 | 50 | 45.9 | 20.1 | 70.6 | 8.4 |
| 85(0.69) | 20 | 40 | 87.8 | 17.7 | 64.0 | 15.3 |

EXAMPLE 5

A further series of experiments was conducted to study the effect of temperature on the catalyst activity and on product selectivity. A 30 cc. charge of 20/30 mesh (0.59 to 0.84 mm.) silica which had been previously treated with boron trifluoride gas under pressure was used in these experiments. The 1-decene containing about 45 ppm. water was fed to the reactor at a rate of 90 cc. per hour (3.0 LHSV hr$^{-1}$) and the boron trifluoride gas was injected at a rate of about 12.0 cc. per minute (3.23 weight percent). The reactor was operated with an outlet pressure of 125 psig. (0.965 MPa). The results are shown in Table V in which the temperature is the hottest temperature measured in the catalyst bed.

TABLE V

| Temp. °C. | Conv. % | Selectivity | | |
|---|---|---|---|---|
| | | $C_{20}$, % | $C_{30}$, % | $C_{40}$, % |
| 14 | 78.6 | 17.2 | 65.1 | 14.3 |
| 25 | 78.9 | 27.0 | 61.3 | 9.8 |
| 36 | 70.8 | 43.6 | 51.6 | 4.6 |
| 44 | 56.3 | 51.5 | 44.5 | 3.6 |

EXAMPLE 6

The effect of variations in the moisture content of the feed 1-decene was studied in a series of experiments. The catalyst used in Example 5 was also used in these experiments and all other reaction conditions were the same except as shown in Table VI which sets out the results of these experiments.

TABLE VI

| H₂O, ppm. | Temp. °C. | Conv. % | Selectivity | | |
|---|---|---|---|---|---|
| | | | C₂₀, % | C₃₀, % | C₄₀, % |
| 12 | 27 | 60.3 | 33.5 | 59.8 | 6.0 |
| 27 | 14 | 79.8 | 26.6 | 63.6 | 9.3 |
| 42 | 27 | 79.3 | 27.3 | 61.3 | 9.6 |
| 80 | 27 | 82.4 | 31.6 | 60.1 | 7.3 |

EXAMPLE 7

A series of experiments was carried out to study the effect on conversion and product selectivity resulting from variations in the flow rate of the 1-decene through the catalyst. The same catalyst as used in Example 2 was used in these experiments subsequent to this earlier experiment. In these experiments the flow rates of the 1-decene and the boron trifluoride injection rates were periodically increased to provide a constant 3.08 weight percent amount of boron trifluoride in the 1-decene in each experiment. The hot spot temperature rose as the feed rate increased as a result of the higher heat generation at increasing feed rates and constant conversion. The results are set out in Table VII.

TABLE VII

| 1-decene, cc/hr. | Temp. °C. | Conv. % | Selectivity | | |
|---|---|---|---|---|---|
| | | | C₂₀, % | C₃₀, % | C₄₀, % |
| 60 | 26 | 84.9 | 38.3 | 54.6 | 7.1 |
| 150 | 31 | 84.1 | 29.9 | 58.4 | 10.0 |
| 240 | 39 | 85.9 | 36.0 | 55.5 | 7.5 |

In the above table the flow of 1-decene was at a liquid hourly space velocity of about one per hour at the start and was increased to about four per hour at the completion for the final experiment.

EXAMPLE 8

This example demonstrated the high activity of a catalyst after 257 hours of reaction time. The catalyst was used over a large number of experiments at many different reaction conditions including a cycle of experiments using pure 1-decene feed followed by a cycle of experiments using a feed stream comprising 1-decene with a dimer fraction. The amount of water in the feed varied from a low of 12 ppm. to a high of 80 ppm. over the series of experiments. The solid adsorbent was 30 cc. of a 20/30 mesh (0.59 to 0.84 mm.) silica.

In the last experiment which used pure 1-decene the 1-decene containing 80 ppm. water was fed to the reactor at a rate of 90 cc. per hour and the boron trifluoride was fed at a rate of 12.0 cc. per minute. The reactor was operated at an outlet temperature of 125 psig. (0.965 MPa). After seven hours of this experiment, which was a total of 148 hours use of the catalyst, at which time the hot spot temperature was 27° C., analysis of the product showed a conversion of 82.4 percent at a selectivity of 31.6 percent to the dimer, 60.1 percent to the trimer and 7.3 percent to the tetramer.

The feed was then switched to a mixture comprising the pure 1-decene and a monomer-dimer product fraction which analyzed 39.9 percent 10-carbon olefin, 15.4 percent 10-carbon paraffin, 43.8 percent dimer and 0.9 percent trimer. In the last experiment an amount of the monomer-dimer product was added to the pure 1-decene to provide a feed stream containing 17 percent dimer. In this final experiment this feed stream which also contained 32 ppm. water was introduced into the reactor at a rate of 30 cc. per hour and the boron trifluoride was fed at the rate of 12.0 cc. per minute. The reactor was operated at an outlet pressure of 125 psig. (0.965 MPa). After 13 hours of this experiment, which was a total of 257 hours use of the catalyst, at which time the hot spot temperature was 16° C., product analysis showed a conversion of 81.5 percent at a selectivity of 19 percent to the dimer, 63.3 percent to the trimer and 17.4 percent to the tetramer.

EXAMPLE 9

In a further series of runs a 30 cc. sample of a 10/20 mesh (0.84 to 2.0 mm.) silica was used as the solid adsorbent. In one experiment 70 cc. of a feed comprising 1-decene, a sufficient amount of the monomer-dimer fraction described in Example 8 to provide 15 percent dimer and 26 ppm. water was introduced into the reactor at a rate of 70 cc. per hour. The boron trifluoride was fed at a rate of 3.10 cc. per minute, which was one percent boron trifluoride in the feed mixture. The hot spot temperature was 11° C. and the outlet pressure was 100 psig. (0.793 MPa). Analysis of the product after four hours at these operating conditions showed a conversion of 85.4 percent at a selectivity of 23.3 percent to dimer, 61.4 percent to trimer and 14.7 percent to tetramer.

EXAMPLE 10

Example 9 was repeated at the same conditions except that the 1-olefin feed rate was 73 cc. per hour and the water content of the feed was 37 ppm. The significant difference was a reduction in the feed rate of the boron trifluoride down to a rate of 1.50 cc. per minute, which was 0.49 percent of the 1-olefin mixture fed to the reactor. After two hours of operation, analysis of the product showed a drop in the conversion down to 67.6 percent at a selectivity of 18.7 percent to the dimer, 67.1 percent to the trimer and 11.7 to the tetramer. Further analysis after operating an additional hour showed that the conversion had further dropped to 50.5 percent without much change in the selectivity.

A comparison of Examples 9 and 10 reveals that at the particular operating conditions used in these experiments one percent boron trifluoride in the feed was sufficient while 0.49 percent was insufficient.

EXAMPLE 11

The series of experiments using the solid adsorbent described in Examples 9 and 10 was concluded by a final experiment which itself was conducted for 57 hours. This experiment was carried out using a feed rate of 75 cc. per hour of the same feed mixture containing 15 percent dimer and 25 ppm. water. The feed rate of the boron trifluoride was 2.70 cc. per minute which amounted to 0.87 percent boron trifluoride in the feed mixture. The reactor was operated at an outlet pressure of 100 psig. (0.793 MPa) and a hot spot temperature of 18° C. Analysis of the product at the end of this experiment, which represented about 400 hours of use of this catalyst over a period of three weeks, showed a conversion of 82.9 percent at a selectivity of 20.4 percent to dimer, 64.1 percent to trimer and 14.9 percent to tetramer.

This final experiment demonstrated that a boron trifluoride concentration as low as 0.87 weight percent in the feed and a moisture level as low as 25 ppm. was adequate to obtain superior aging characteristics and stability. It was further observed that the hot spot remained at the entrance of the silica bed for the entire 57 hours of the experiment, which indicated that most of the conversion took place at the inlet of the catalyst bed and that there was, therefore, no signs of aging.

It is to be understood that the above disclosure is by way of specific example and that numerous modifications and variations are available to those of ordinary skill in the art without departing from the true spirit and scope of the invention.

We claim:

1. A three-component hydrocarbon conversion catalyst comprising particulate silica having boron trifluoride and water adsorbed thereon, said catalyst obtainable by the adsorption on said particulate silica of water and boron trifluoride from a liquid hydrocarbon in the presence of an atmosphere comprising boron trifluoride.

2. A three-component catalyst in accordance with claim 1 in which the silica has a particle size of between about 3 and about 400 mesh.

3. A three-component catalyst in accordance with claim 2 in which the partial pressure of boron trifluoride in said atmosphere is between about atmospheric pressure and about 1,000 psig.

4. A three-component catalyst in accordance with claim 3 in which the water is present in the liquid hydrocarbon in an amount of between about 5 and about 130 ppm.

5. A three-component catalyst in accordance with claim 1 in which the silica has a particle size of between about 10 and about 50 mesh.

6. A three-component catalyst in accordance with claim 2 in which the partial pressure of boron trifluoride in said atmosphere is between about 10 and about 250 psig.

7. A three-component catalyst in accordance with claim 6 in which the water is present in the liquid hydrocarbon in an amount of between about 20 and about 100 ppm.

* * * * *